United States Patent [19]
Vashi et al.

[11] Patent Number: 4,701,447
[45] Date of Patent: Oct. 20, 1987

[54] N-((2-NITRO)PHENYL)-N' (ORGANIC ACID) GUANIDINE ANTHELMINTICS

[75] Inventors: Dhiru B. Vashi, Wharton; Jeffrey N. Clark, New Egypt; Neil A. Lindo, New Providence, all of N.J.

[73] Assignee: Schering Corporation, Kenilworth, N.J.

[21] Appl. No.: 535,445

[22] Filed: Sep. 23, 1983

[51] Int. Cl.[4] ............... A01N 43/54; A01N 41/02; C07C 141/16; C07C 143/55
[52] U.S. Cl. ............................ 514/85; 560/34; 560/13; 560/9; 558/176; 558/29; 549/473; 549/472; 549/72; 549/68; 548/197; 546/328; 546/315; 546/306; 546/264; 546/262; 544/386; 544/382; 544/359; 544/335; 544/323; 544/296; 514/576; 514/517; 514/132; 514/131; 514/129; 514/99; 514/95; 514/92; 514/89; 514/86

[58] Field of Search ............... 546/306, 315, 328, 262, 546/264; 544/323, 335, 296, 359, 382, 386; 548/197; 549/68, 72, 472, 473; 558/29, 176; 560/13, 34, 9; 260/506, 502.5 D; 514/576, 517, 85, 86, 89, 92, 95, 99, 129, 132, 131

[56] References Cited

U.S. PATENT DOCUMENTS

| 4,217,358 | 8/1980 | Haugwitz | 424/274 |
| 4,246,260 | 1/1981 | Kölling et al. | 424/228 |
| 4,293,569 | 10/1981 | Haugwitz et al. | 424/300 |
| 4,348,406 | 9/1982 | Varchei | 424/300 |
| 4,406,893 | 9/1983 | Varchei | 424/199 |
| 4,435,398 | 3/1984 | Varchei | 424/250 |

Primary Examiner—Nicky Chan
Attorney, Agent, or Firm—John J. Maitner; Stephen I. Miller; James R. Nelson

[57] ABSTRACT

This invention relates to organic acid-substituted guanidine compounds. Also disclosed are methods for preparing the compounds, compositions containing them, and methods for their use as anthelmintics.

11 Claims, No Drawings

N-((2-NITRO)PHENYL)-N' (ORGANIC ACID) GUANIDINE ANTHELMINTICS

SUMMARY

This invention relates to novel organic acid substituted guanidine compounds, to methods for preparing and using them, and to compositions containing them. Compounds of the invention have anthelmintic activity.

DETAILED DESCRIPTION

The compounds of the present invention are represented by the formula

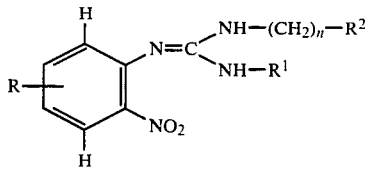   I and the pharmaceutically acceptable salts thereof, wherein
R is hydrogen, $-OR^3$, $-S(O)_mR^3$,

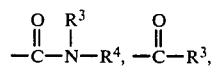

halogen or $-CF_3$;
$R^1$ is hydrogen,

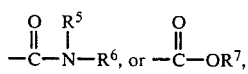

with the proviso that when $R^1$ is

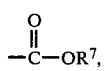

R is not loweralkylthio;
$R^2$ is $-SO_3H$, $-OSO_3H$, $-COOH$, $-PO_3H_2$, or $-OPO_3H_2$;
$R^3$ and $R^4$ are independently hydrogen, loweralkyl, loweralkoxyloweralkyl, hydroxyloweralkyl, cycloloweralkyl, phenyl or substituted phenyl, benzyl or substituted benzyl (wherein there are 1, 2 or 3 substituents on the substituted phenyl or substituted benzyl independently selected from halogen, loweralkyl, loweralkoxy, haloloweralkyl, or loweralkoxyloweralkyl), or 5 or 6 membered heterocycles having 1 or 2 heteroatoms independently selected from oxygen, nitrogen and sulfur;
$R^5$, $R^6$ and $R^7$ are independently hydrogen, loweralkyl, loweralkoxyloweralkyl, hydroxyloweralkyl, phenyl or substituted phenyl, and benzyl or substituted benzyl (wherein there are 1, 2 or 3 substitutents on the substituted phenyl or substituted benzyl independently selected from halogen, loweralkyl, loweralkoxy, haloloweralkyl, or loweralkoxyloweralkyl);
n is 1 to 6; and
m is 0, 1 or 2; with the further proviso that when R is $OR^3$ or loweralkylthio and $R^1$ is

$R^2$ is not $-COOH$.

As used herein, "lower alkyl" means straight or branched alkyl chains of 1 to 6 carbon atoms, e.g. methyl, ethyl, n-propyl, n-butyl, iso-butyl, and hexyl. Similarly, "lower alkoxy" means alkoxy groups having 1 to 6 carbon atoms, e.g. methoxy, ethoxy, propoxy, iso-butoxy, and pentoxy. "Cycloloweralkyl" means alkyl rings of 3 to 6 members, i.e. cyclopropyl, cyclobutyl, cyclopentyl, and cyclohexyl. "Halogen" means fluorine, chlorine, bromine and iodine. "Haloloweralkyl" means loweralkyl groups substituted by 1 to 3 halogen atoms, e.g. trifluoromethyl, dichloromethyl and chloroethyl.

Examples of heterocycles defined in $R^3$ and $R^4$ are pyridine, furan, thiophene, pyrimidine, piperazine and thiazole. All positional isomers are contemplated, e.g., 2-, 3-, and 4-pyridine, 2- and 3-furan.

The pharmaceutically acceptable salts contemplated include metal salts, e.g. alkali and alkali earth metal salts such as sodium, potassium and calcium, and other physiologically acceptable salts, e.g. trisamine, alkyl ammonium salts such as N-methylglucamine, ethanolamine, diethanolamine, triethanolamine, pyridinium and procaine, and tetralkylammonium salts such as those produced with tetramethylammonium or tetraethylammonium ions.

Also included within the scope of the invention are the tautomers at the guanidine group, i.e.

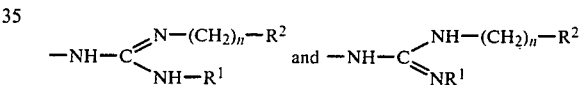

Preferred compounds are those wherein R is $-S(O)_mR^3$ and wherein the loweralkylthio, sulfinyl or sulfonyl substituent is in the 5-position of the phenyl ring. Also preferred are compounds wherein $R^1$ is

A third group of preferred compounds are those wherein $R^2$ is $-SO_3H$ and n is 2 or 3.

The compounds of this invention can be prepared as follows according to procedures generally known in the art for preparing similar compounds.

A convenient intermediate for the preparation of compounds of formula I is an N-lower-alkoxycarbonyl-N'-[(2-nitro-(4- or 5-)substituted)phenyl]-N''-(alkylacid)guanidine, i.e. a compound of the formula

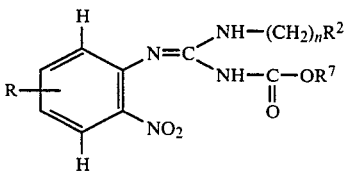   II

N-alkoxycarbonyl compounds of formula II can be hydrolyzed according to well known procedures (e.g. with a base such as sodium hydroxide in a solvent such as water or methanol) to prepare the corresponding (alkyl acid)guanidines (i.e. the

group is replaced by H).

(Alkylacid)guanidines can be treated with a diloweralkylcarbamyl chloride, e.g. dimethyl carbamyl chloride, according to techniques known in the art to obtain the corresponding N-[diloweralkylcarbamyl]-N'-[(2-nitro-(4- or 5-)substituted)phenyl]-N''-(alkylacid)guanidine.

N-[loweralkylcarbamyl]homologs, e.g. methylcarbamyl compounds, can be prepared by treating (alkylacid)guanidines with potassium cyanate followed by alkylation with diloweralkyl sulfate, e.g. dimethylsulfate, or lower alkyl halide, e.g. methyl chloride or methyl bromide. Alternatively, alkylcarbamyl compounds can be prepared by treating (alkylacid)guanidines or the sodium salts thereof with alkyl isocyanate.

N-[carbamyl] compounds can also be prepared from (alkylacid)guanidines by treatment with potassium cyanate followed by treatment with acid such as hydrochloric, acetic or sulfuric acid.

Compounds of formula II are prepared by treating appropriately substituted 2-nitroaniline with a carboalkoxyisothiocyanate, reacting the resulting product with a base such as sodium hydride or sodium methoxide and a dialkylsulfate or an alkylhalide to obtain the S-alkyl-isothiourea which is then reacted with an Ω-aminoalkylacid (e.g. taurine or 4-aminobutyrate) and a base such as sodium hydroxide. The reaction scheme is shown below:

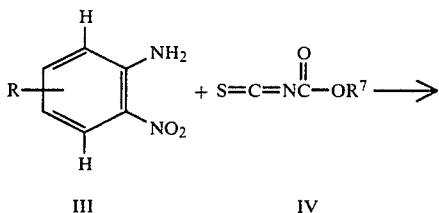

-continued

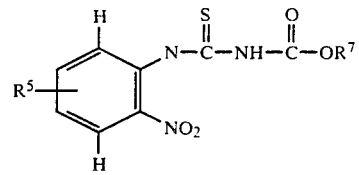

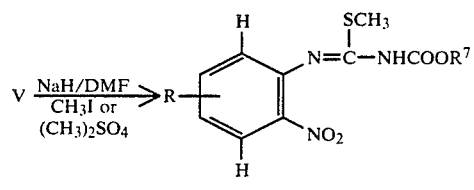

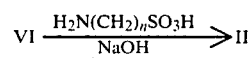

Compounds of formula III are either known in the art, or may be prepared by methods well known to those skilled in the art.

Preferred compounds of formula I wherein R is —S-$(O)_mR^3$ may be prepared by well known procedures from the corresponding —$SR^3$ compounds by treating the thio substituent with an oxidizing agent such as m-chloroperbenzoic acid, sodium m-periodate or hydrogen peroxide in acetic acid. Amino groups in the starting material may be protected during the oxidation by the addition of a reagent such as trifluoroacetic acid. Treatment with one equivalent of oxidizing agent will yield the —$SOR^3$ (sulfinyl) compound while treatment with two equivalents will yield the —$SO_2R^3$ compound (sulfonyl). This oxidation may be carried out at one of several stages in the preparation of the compound as shown below, wherein the preparation of a sulfinyl compound is described:

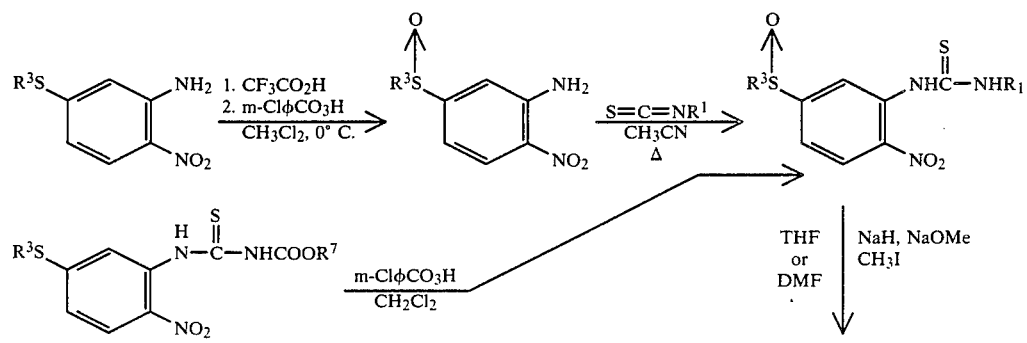

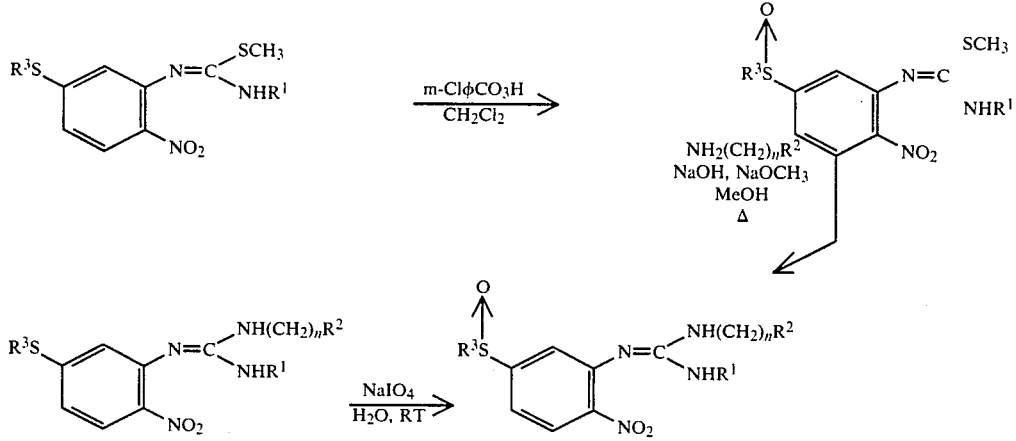

Metal salts, alkyl ammonium salts and other pharmaceutically acceptable salts may be prepared according to methods well known to those skilled in the art.

The following examples illustrate the preparation of compounds and compositions of this invention.

EXAMPLE 1

N-[(2-Nitro-5-propylthio)phenyl]-N'-(2-ethyl sulfonic acid)guanidine

Combine N-methoxycarbonyl-N'-[(2-nitro-5-propylthio)phenyl]-N"-(2-ethyl sulfonic acid)guanidine (42.1 g) and sodium hydroxide (17.6 g of a 50% solution) in water (420 ml) and reflux for 4 hours. Cool the resulting solution and acidify to pH 1-2 with 10N aqueous hydrochloric acid. Filter the resulting precipitate, wash with cold water (3×100 ml) then methanol (2×100 ml) and dry to obtain the title compound, m.p. 250°-253° C. (dec).

EXAMPLE 2

N-(N'''-dimethylcarbamyl)-N'-[(2-nitro-5-propylthio)-phenyl]-N"-(2-ethyl sulfonic acid)guanidine Suspend the product of Example 1 (3.62 g) in anhydrous dimethylformamide (100 ml), add sodium methoxide (0.54 g) and warm gently with stirring to make a homogenous solution. Add N,N-dimethyl carbamoyl chloride and heat at 80° C. for 8 hours. Cool the resultant mixture at room temperature, pour into water (100 ml) and stir 1 hour. Filter the resulting solid, wash the filtrate with cold acetone and dry the filtrate to obtain the title compound.

Alternatively, the title compound may be prepared as follows:

Combine potassium thiocyanate (10.2 g) and dimethyl carbamoyl chloride (10.7 g) in anhydrous acetonitrile (250 ml) and reflux for 8 hours. Filter the resulting mixture and combine the filtrate with 2-nitro5-propylthioanaline (14.2 g) and reflux for 8 hours. Evaporate the solvent and dissolve the resultant residue in anhydrous dimethylformamide (100 ml). Cool the solution to 0°-5° C. and add sodium hydride (2.0 g) followed by iodomethane (30 g, then reflux again for 8 hours. Cool the resultant mixture to room temperature, filter and add the sodium salt of taurine, stir for 4 hours, then filter the resulting precipitate to obtain the title compound.

EXAMPLE 3

N-Methoxycarbonyl-N'-[(2-nitro-5-propylsulfinyl)-phenyl]-N"-(2-ethyl sulfonic acid)guanidine sodium salt

Method A

Dissolve N-methoxycarbonyl-N'-[(2-nitro-5-propylthio)phenyl]-N"(2-ethyl sulfonic acid)guanidine sodium salt (4.43 g) in water (70 ml) at about 15° C., add sodium meta periodate (2.25 g) and stir at room temperature until thin layer chromatography (elute in 20% methanol in chloroform) indicates that no starting material is left. Evaporate the water and extract the resultant residue with warm methanol. Evaporate the methanol, dissolve the crude material in methanol, filter, pour the filtrate into stirred ether (1 liter), then collect and dry the precipitate to obtain the title compound, m.p. 125°-135° C.

Method B

1. Cool to 0°-5° C. a stirred solution of 2-nitro-5-propylthioaniline (21.2 g) in methylene chloride (350 ml) and add trifluoroacetic acid (11.40 g), followed by the dropwise addition of 85% m-chloroperbenzoic acid (22.34 g) in methylene chloride (450 ml). Stir 30 minutes at 0° C., then warm to room temperature and stir 3.5 hours. Add chloroform to dissolve the solids, and extract the mixture with 10% sodium carbonate solution three times, extract with water once, filter over magnesium sulfate, then evaporate the organic solvent in vacuo. Recrystallize the residue from methanol to obtain 2-nitro-5-propylsulfinylaniline, m.p. 128°-130° C.

2. Dissolve potassium thiocyanate (14.6 g) in acetonitrile (450 ml), add methyl chloroformate (14.2 g) and stir at room temperature for 2 hours to obtain carboxymethoxy isothiocyanate. Add to this solution a slurry of the product of step 1 (17.1 g) in acetonitrile (400 ml), stir the resulting mixture for 1 hour at room temperature, then reflux about 24 hours. Filter the solution hot to remove potassium chloride, then evaporate the acetonitrile in vacuo. Recrystallize the resultant residue from methanol to obtain N-methoxycarbonyl-N'-[(2-nitro-5-propylsulfinyl)phenyl]thiourea, m.p. 150°-152° C.

3. To a stirred slurry of 50% sodium hydride dispersion (3.02 g) in tetrahydrofuran (THF) (50 ml) at 5°-10° C., add dropwise a solution of the product of step 2 (20.72 g) in THF (250 ml). When gas evolution subsides, add methyl iodide (10.22 g) and allow to come to room temperature. Reflux 4 hours, then evaporate the solvent and partition the resultant residue between water (neutralize with hydrochloric acid) and chloroform. Dry the organic phase over MgSO$_4$ and evaporate the solvent. Triturate, then recrystallize the resultant product from methanol to obtain N-methoxycarbonyl-N'-[(2-nitro-5-propylsulfinyl)-phenyl]-S-methyl isothiourea, m.p. 130°–133° C.

4. To a solution of the product of step 3 (10.8 g) in methanol (300 ml), add taurine (7.51 g) and sodium hydroxide (2.4 g) and stir for about two weeks at room temperature. Evaporate the solvent in vacuo, then partition the residue between water and chloroform. Separate the aqueous layer and evaporate the water at room temperature under a stream of air, then dry further under vacuum. Dissolve the resultant residue in methanol, filter and pour the filtrate into stirred ether (1 liter). Filter the resulting solid and dry to obtain the title compound, m.p. 115°–120° C.

Method C

1. Add 85% m-chloroperbenzoic acid (8.53 g) in methylene chloride (200 ml) dropwise to a 0°–5° C. stirred solution of N-methoxycarbonyl-N'''[(2-nitro-5-propylthio)phenyl]-S-methylisothiourea (13.72 g) in methylene chloride (150 ml). Allow the solution to warm to room temperature and stir overnight. Extract the resultant mixture with 10% sodium carbonate solution, wash the organic layer with water, dry over MgSO$_4$ and concentrate in vacuo. Recrystallize the resultant residue from methanol to obtain N-methoxycarbonyl-N'-[(2-nitro-5-propylsulfinyl)phenyl]-5-methyl isothiourea, m.p. 127°–130° C.

2. Treat the product of step 1 in a manner similar to that described in Method B, step 4, to obtain the title compound.

Using the methods described above, the following compounds also can be prepared:

N-methoxycarbonyl-N'-[(2-nitro-(4 or 5)-propylsulfonyl)phenyl]-N''-(2-ethyl sulfonic acid)guanidine;

N-methoxycarbonyl-N'-[(2-nitro-(4 or 5)-propylsulfinyl)phenyl]-N''-(3-propyl sulfonic acid)guanidine;

N-ethoxycarbonyl-N'-[(2-nitro-(4 or 5)-cyclopropylthio)phenyl]-N''-(2-ethyl sulfonic acid)guanidine;

N-carbamyl-N'-[(2-nitro-(4 or 5)-(3-ethoxy)propylthio)phenyl]-N''-(2-ethyl sulfonic acid)guanidine;

N-methoxycarbonyl-N'-[(2-nitro-(4 or 5)-(3-hydroxy)propylthio)-phenyl]-N''-(2-ethyl carboxylic acid)guanidine;

N-carbamyl-N'-[(2-nitro-(4 or 5)-phenylthio)phenyl]-N''-(2-ethyl sulfonic acid)guanidine;

N-(2-hydroxyethylcarbamyl)-N'-[(2-nitro-(4 or 5)-4-chlorophenylthio)phenyl]-N''-(2-ethyl sulfonic acid)guanidine;

N-methoxyethylcarbamyl-N'-[(2-nitro-(4 or 5)-(2,3 or 4-methoxybenzyl)thio)-phenyl]-N''-(2-ethyl sulfonic acid)guanidine;

N-methoxycarbonyl-N'-[(2-nitro-(4 or 5)-2-pyridylthio)phenyl]-N''-(2-ethyl carboxylic acid)guanidine;

N-phenoxycarbonyl-N'-[(2-nitro-(4 or 5)-(4-trifluoromethylphenyl)thio)phenyl]-N''-(2-ethyl sulfonic acid)guanidine;

N-[(N'''-methyl-N'''-benzyl)carbamyl]-N'-[(2-nitro-(4 or 5)-butylsulfinyl)-phenyl]-N''-(2-ethyl hydrogen sulfate)guanidine;

N-methoxycarbonyl-N'-[(2-nitro-(4 or 5)-trifluoromethylphenyl]-N''-(2-ethyl sulfonic acid)guanidine;

N-carbamyl-N'-[(2-nitrophenyl)]-N''-(2-ethyl sulfonic acid)guanidine;

N-(4-chlorobenzyloxycarbonyl)-N'-(2-nitro-(4 or 5)-chlorophenyl)-N''-(2-ethyl phosphoric acid)guanidine;

N-dimethylcarbamyl-N'-[(2-nitro-(4 or 5)-propoxy)phenyl]-N''-(2-ethyl sulfonic acid)guanidine;

N-[N'''-methyl-N'''-ethyl)carbamyl]-N'-[(2-nitro-(4 or 5)-(3-hydroxypropyloxy))phenyl]-N''-(2-ethyl sulfonic acid)guanidine;

N-carbamyl-N'-[(2-nitro-(4 or 5)-amidophenyl)]-N''-(2-ethyl sulfonic acid)guanidine;

N-methoxyethylcarbamyl-N'-[(2-nitro-(4 or 5)-4-acetylphenyl)]-N''-(2-ethyl sulfonic acid)guanidine; and N-methoxycarbonyl-N'-[(2-nitro-(4 or 5)-propylthio)phenyl]-N''-(3-propyl sulfonic acid)guanidine.

The compounds of the present invention are useful in combatting helminthiasis, i.e. in treating animals, including humans, suffering from an infestation of parasitic worms, for example, roundworms, hookworms, whipworms or tapeworms, by administering to the host animal a therapeutic amount of a compound of the present invention.

The compounds of this invention exhibit significant anthelmintic effects when administered to a host (e.g. a human, swine, dog, bird or ruminant) at doses as low as about one milligram per kilogram of body weight to about one hundred fifty milligrams per kilogram in a single day dosing or over several days, according to techniques well known in the art. A preferred method is to administer the compound at 5 to 25 milligrams per kilogram in a single dose.

The optimum dose for each species of animal and for each type of parasite can readily be determined by one skilled in the art of using standard techniques such as the Modified McMaster Egg Counting Technique as described by H. B. Whitlock and H. McL. Gordon, J. Council Scientific Industrial Research (Australia) 12, p. 50, 1939 and H. B. Whitlock, J. Council Scientific Research (Australia) 21, p. 177, 1948.

From these, and similar tests, anthelmintic efficacy is assessed by determining the number of eggs in feces passed on the days following treatment with the compound compared with pretreatment days. Based on experimentation, proper dosages for curing various infections can be determined.

Compounds of this invention may be administered in various formulations well known to those skilled in the human and veterinary medical arts, e.g., suspensions, solutions, capsules, tablets and injectable preparations. In addition, for veterinary use, the compounds may be administered as feed or drinking water additive preparations.

For injectable preparations, the active ingredient is admixed with suitable sterile carriers such as sterile water and isotonic saline solution.

Suitable clinical formulations containing the compounds of this invention can be administered orally in the form of tablets, capsules, elixirs and the like. The active compound is compounded with inert carriers such as, for example, gums, starches and sugars or it may be incorporated into gelatin capsules or formulated into elixirs which have the advantage of being amenable to manipulations in flavor by the addition of flavoring agents.

Anthelmintic formulations particularly useful for, but not limited to, veterinary use comprise the compounds of this invention in ready to use liquid suspensions or wettable or water-dispersible powders which are mixed with water prior to use.

The following examples show particularly useful formulations. In the examples, the term "Drug" refers to N-(N'''-dimethylcarbamyl)-N'-[(2-nitro-5-propylthio)phenyl]-N''-(2-ethyl sulfonic acid)guanidine. It will be appreciated by those skilled in the art that an equivalent amount of another compound of formula I may be substituted for the named compound.

A. Liquid-suspension formulation:

A liquid-suspension formulation may contain from 50 to 55% w./v. (grams/liters) of the active compound together with a dispersing agent and stabilizing agent. A typical formulation is as follows:

| Drug | 50 to 55 parts by weight |
|---|---|
| Dispersing agent | ½ to 2 parts by weight |
| Stabilizing agent | 1 to 3 parts by weight |
| Preservative | as required |
| Water | Sufficient to make 100 volumes. |

Suitable dispersing agents are those containing sulphonate groups, for example sodium lignin sulphonate, or the sulphonated phenol or naphthol formaldehyde polymers. Bentonite may be employed as the stabilizing agent, although it is possible to use such protective colloids as carboxymethyl cellulose, sodium alginate and the like. The formulations can be prepared by mixing the active compound and water containing dissolved dispersing agents very vigorously by means of suitable mechanical mixing equipment.

B. Powder formulation:

A wettable or water-dispersible powder formulation may contain about 90 to 95% w./w. of the active compound together with a wetting agent and dispersing agent. A diluent such as kaolin can also be added if a concentration below about 98% w./w. is required. An anti-foaming agent and, in some cases, a stabilizing agent may be present. A typical formulation is as follows:

| Drug | 90 to 95 parts by weight |
|---|---|
| Wetting agent | ½ to 4 parts by weight |
| Stabilizing agent | 0 to 2 parts by weight |
| Anti-foaming agent | 0.01 to 1 by weight |
| Water | 0 to 5 by weight |

Suitable wetting agents are the non-ionic alkylphenolethylene oxide adducts, such as an octylphenol or nonylphenol condensed with ten moles of ethylene oxide, or anionic materials, such as the synthetic aryl alkyl sulphonates, or sodium dibutyl napthalene sulphonate. In general, about 1% w./w. wetting agent is required. The anti-foaming agent employed may be either a silicone or such materials as ethyl hexanol, octanol and the like; and the stabilizing agent may be chosen from bentonite or the water-soluble gums as discussed above. Wettable or water-dispersible powder formulations are prepared by careful and adequate mixing of the active compound with other ingredients with or without the addition of some water using typical powder blending equipment such as a ribbon blender. The powder is stirred into water by the user before application in the field.

| C. Tablet formulation | Grams per 1000 tablets |
|---|---|
| Drug | 200.0 |
| Lactose | 90.0 |
| Dicalcium phosphate, hydrous | 122.5 |
| Polyvinylpyrolidone | 25.0 |
| Polyethyleneglycol 1500 | 7.5 |
| Corn Starch | 50.0 |
| Magnesium Stearate | 5.0 |
| | 500.0 |

Mix the active compound, the lactose and the dicalcium phosphate. Dissolve the polyethyleneglycol 1500 and the polyvinylpyrrolidone in approximately 20 ml of water. Granulate the powder blend with the water solution, adding additional water if necessary, to product a damp mass. Pass the wet granulation through a 12 mesh screen; spread on trays and air dry at 35° C. Blend the dry granulates with the starch and the magnesium stearate. Compress into 500 mg tablets.

| D. Capsule formulation | Grams per 1000 capsules |
|---|---|
| Drug | 200.0 |
| Lactose | 198.0 |
| Magnesium Stearate | 2.0 |
| | 400.0 |

Blend the ingredients and fill into hard gelatine capsules

| E. Injectable formulation | mg/ml |
|---|---|
| Drug | 50.0 |
| Polyethylene Glycol 400 | 500.0 |
| Dimethyl Acetamide | 300.0 |
| Benzyl Alcohol | 20.0 |
| Water for Injection to q.s. | 1.0 ml |

Combine the above ingredients using standard techniques.

We claim:

1. A compound represented by the formula

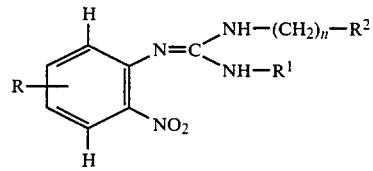

and the pharmaceutically acceptable salts thereof, wherein

R is

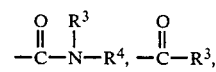

halogen or —CF$_3$;

R$^1$ is hydrogen,

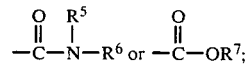

R$^2$ is —SO$_3$H, —OSO$_3$H, —PO$_3$H$_2$, OR —OPO$_3$H$_2$;

R$^3$ and R$^4$ are independently hydrogen, loweralkyl, loweralkoxyloweralkyl, hydroxyloweralkyl, cycloloweralkyl, phenyl or substituted phenyl, benzyl or substituted benzyl (wherein there are 1, 2 or 3 substituents on the substituted phenyl or substituted benzyl independently selected from halogen, loweralkyl, loweralkoxy, haloloweralkyl, or loweralkoxyloweralkyl, or 5 or 6 membered heterocycles having 1 or 2 heteroatoms independently selected from oxygen, nitrogen and sulfur where such heterocycles are bonded to the molecule through a carbon atom;

$R^5$ and $R^6$ are independently hydrogen, loweralkyl, loweralkoxyloweralkyl, hydroxyloweralkyl, phenyl or substituted phenyl, and benzyl or substituted benzyl (wherein there are 1, 2 or 3 substituents on the substituted phenyl or substituted benzyl independently selected from halogen, loweralkyl, loweralkoxy, haloloweralkyl, or loweralkoxyloweralkyl);

$R^7$ is phenyl or substituted phenyl, benzyl or substituted benzyl (wherein there are 1, 2 or 3 substituents on the substituted phenyl or substituted benzyl independently selected from halogen, loweralkyl, loweralkoxy, haloloweralkyl and loweralkoxyloweralkyl); and n is 1 to 6.

2. A compound of claim 1 where R is

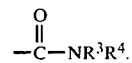

3. A compound of claim 1 where R is

4. A compound of claim 1 where R is halogen or —CF$_3$.

5. A compound of claim 1 where $R^1$ is

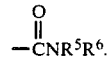

6. A compound of claim 1 where R is halogen.

7. A compound of claim 1 where $R^2$ is —SO$_3$H.

8. A composition comprising an anthelmintically effective amount of a compound of claim 1 and a pharmaceutically acceptable carrier.

9. A method of treating helminth infestation in mammalian or avian species which comprises administering to an helminth infested animal an anthelmintically effective amount of a compound of claim 1.

10. The method of treating helminth infestation in mammalian or avian species which comprises administering to an helminth infested animal a composition of claim 8.

11. A compound of claim 1 where the heterocycles are selected from pyridine, furan, thiophene, pyrimidine, piperazine and thiazole.

* * * * *